(12) United States Patent
Lim et al.

(10) Patent No.: US 11,819,631 B2
(45) Date of Patent: Nov. 21, 2023

(54) CATHETER SHAFT AND ASSOCIATED DEVICES, SYSTEMS, AND METHODS

(71) Applicant: Covidien LP, Mansfield, MA (US)

(72) Inventors: Elaine Lim, Mountain View, CA (US); Ting Tina Ye, Mountain View, CA (US)

(73) Assignee: Covidien LP, Mansfield, MA (US)

( * ) Notice: Subject to any disclaimer, the term of this patent is extended or adjusted under 35 U.S.C. 154(b) by 61 days.

(21) Appl. No.: 17/491,022

(22) Filed: Sep. 30, 2021

(65) Prior Publication Data

US 2022/0016391 A1 Jan. 20, 2022

Related U.S. Application Data

(63) Continuation of application No. 14/852,268, filed on Sep. 11, 2015, now abandoned.

(51) Int. Cl.
*A61M 25/00* (2006.01)
*A61M 25/01* (2006.01)

(52) U.S. Cl.
CPC .... *A61M 25/0054* (2013.01); *A61M 25/0053* (2013.01); *A61M 25/0108* (2013.01)

(58) Field of Classification Search
CPC .......... A61M 25/0054; A61M 25/0053; A61M 25/0045
See application file for complete search history.

(56) References Cited

U.S. PATENT DOCUMENTS

| | | |
|---|---|---|
| 4,898,591 A | 2/1990 | Jang et al. |
| 4,981,478 A * | 1/1991 | Evard .................. A61M 25/005 600/585 |

(Continued)

FOREIGN PATENT DOCUMENTS

| | | |
|---|---|---|
| CN | 2889337 | 4/2007 |
| CN | 101321552 A | 12/2008 |

(Continued)

OTHER PUBLICATIONS

Examination Report from counterpart European Application No. 15771365.2, dated Jun. 10, 2021, 45 pp.

(Continued)

*Primary Examiner* — Nathan R Price
*Assistant Examiner* — Courtney B Fredrickson
(74) *Attorney, Agent, or Firm* — Shumaker & Sieffert, P.A.

(57) ABSTRACT

Systems, devices, and methods for detaching an implantable device from a delivery system are disclosed herein. One aspect of the present technology, for example, is directed toward an elongated shaft having an inner surface that defines a lumen that extends distally from the proximal portion to an opening at a distal terminus of a distal portion. In some embodiments the distal portion includes an inner polymer structure having a first portion and a second portion positioned distal of the first portion along the length of the inner polymer structure. The first portion can have a first stiffness and the second portion can have a second stiffness less than the first stiffness. The distal portion can further include an outer polymer structure disposed around the inner polymer structure and a coil wound around the inner polymer structure and disposed within the outer polymer structure.

17 Claims, 4 Drawing Sheets

(56) References Cited

U.S. PATENT DOCUMENTS

| | | |
|---|---|---|
| 5,569,220 A | 10/1996 | Webster et al. |
| 5,606,981 A | 3/1997 | Tartacower et al. |
| 5,662,622 A | 9/1997 | Gore et al. |
| 5,702,373 A | 12/1997 | Samson |
| 5,891,114 A | 4/1999 | Chien et al. |
| 5,911,715 A | 6/1999 | Berg et al. |
| 6,508,806 B1 | 1/2003 | Hoste et al. |
| 6,726,712 B1 | 4/2004 | Raeder-Devens et al. |
| 7,507,229 B2 | 3/2009 | Hewitt et al. |
| 7,727,187 B2 | 6/2010 | Lentz |
| 8,206,343 B2 | 6/2012 | Racz |
| 8,636,716 B2 | 1/2014 | Griffin et al. |
| 8,652,193 B2 | 2/2014 | Dorn |
| 8,721,624 B2 | 5/2014 | Wilson et al. |
| 2002/0022825 A1 | 2/2002 | Saitou et al. |
| 2002/0156460 A1 | 10/2002 | Ye et al. |
| 2004/0176740 A1 | 9/2004 | Chouinard |
| 2006/0030835 A1 | 2/2006 | Sherman et al. |
| 2006/0089618 A1 | 4/2006 | McFerran et al. |
| 2007/0043333 A1 | 2/2007 | Kampa et al. |
| 2008/0009831 A1 | 1/2008 | Griffin |
| 2010/0030165 A1 | 2/2010 | Takagi et al. |
| 2010/0249824 A1 | 9/2010 | Kishida et al. |
| 2011/0112514 A1 | 5/2011 | McFerran et al. |
| 2011/0238041 A1 | 9/2011 | Lim et al. |
| 2014/0058257 A1 | 2/2014 | Stigall et al. |
| 2014/0200441 A1 | 7/2014 | Potter et al. |
| 2015/0314108 A1 | 11/2015 | Kanemasa et al. |
| 2016/0001040 A1 | 1/2016 | Yamaguchi et al. |
| 2017/0072163 A1 | 3/2017 | Lim et al. |
| 2017/0072165 A1 | 3/2017 | Lim et al. |

FOREIGN PATENT DOCUMENTS

| | | |
|---|---|---|
| CN | 101588834 | 11/2009 |
| CN | 103635224 | 3/2014 |
| CN | 104853801 A | 8/2015 |
| EP | 0661072 A1 | 7/1995 |
| EP | 0744977 B1 | 3/2003 |
| EP | 0808637 B1 | 3/2004 |
| EP | 2174685 A1 | 4/2010 |
| JP | 2001190681 | 7/2001 |
| JP | 2001218851 | 8/2001 |
| JP | 2006223728 | 8/2006 |
| JP | 2007236472 | 9/2007 |
| JP | 2008517652 | 5/2008 |
| WO | 2000074759 A1 | 12/2000 |
| WO | 2003/086519 A1 | 10/2003 |
| WO | 2006047169 A1 | 4/2006 |
| WO | 2008083104 | 7/2008 |
| WO | 2013003835 | 1/2013 |
| WO | 20140136937 | 9/2014 |
| WO | 20140189828 | 11/2014 |
| WO | 2017044129 A1 | 3/2017 |
| WO | 2017044131 A1 | 3/2017 |

OTHER PUBLICATIONS

Notice of Reasons for Rejection dated Jun. 6, 2019, and translation thereof, from counterpart Japanese Application No. 2018-533033, 11 pp.
Response to Communication Pursuant to Rules 161(1) and 162 EPC dated Apr. 18, 2018 from counterpart European Application No. 15771365.2, filed Oct. 11, 2018, 78 pp..
Second Office Action, and translation thereof, from counterpart Chinese Application No. 201580084442.1, dated Jan. 26, 2021, 24 pp.
Final Office Action and translation thereof, from counterpart Japanese Application No. 2018-533033, dated Sep. 14, 2020, 2 pp.
International Application No. PCT/US2015/049790, International Search Report & Written Opinion, dated May 20, 2016, 17 pages.
International Application No. PCT/US2015/049801, International Search Report & Written Opinion, dated May 12, 2016, 13 pages.
Notification of First Office Action, and translation thereof, from counterpart Chinese Patent Application No. 201580084442.1, dated May 20, 2020, 26 pp.
Second Office Action, and translation thereof, from counterpart Chinese Application No. 201580084514.2, dated Oct. 16, 2020, 13 pp.
The Notification of Rejection, and translation thereof, from counterpart Japanese Application No. 2018-533033, dated Jun. 6, 2019, 11 pp.
The Notification of Rejection, and translation thereof, from counterpart Japanese Application No. 2018-533033, dated Mar. 2, 2020, 7 pp.
Prosecution History from U.S. Appl. No. 14/852,268, dated Feb. 24, 2017 through Jul. 30, 2021, 277 pp.
Response to Communication Pursuant to Article 94(3) EPC dated Jun. 10, 2021, from counterpart European Application No. 15771365.2 filed Dec. 8, 2021, 74 pp.

* cited by examiner

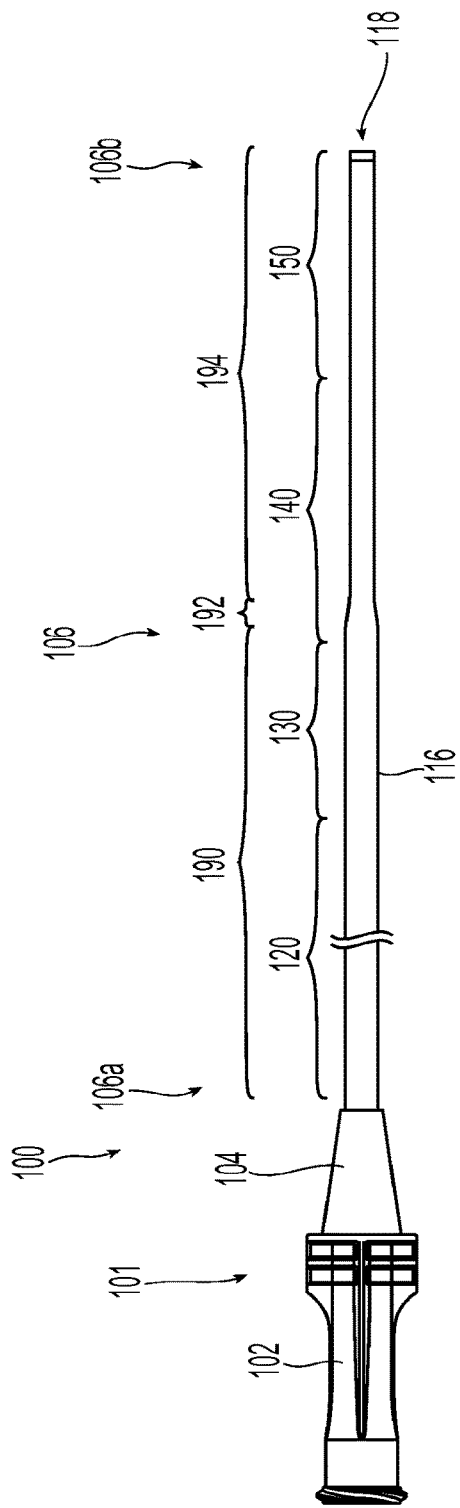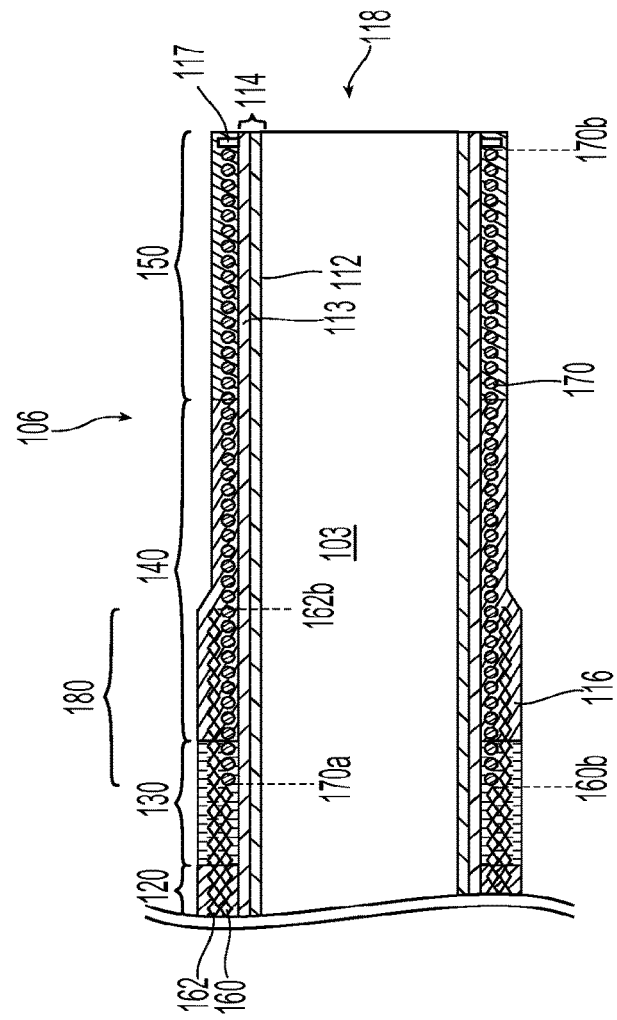
Fig. 1A
Fig. 1B

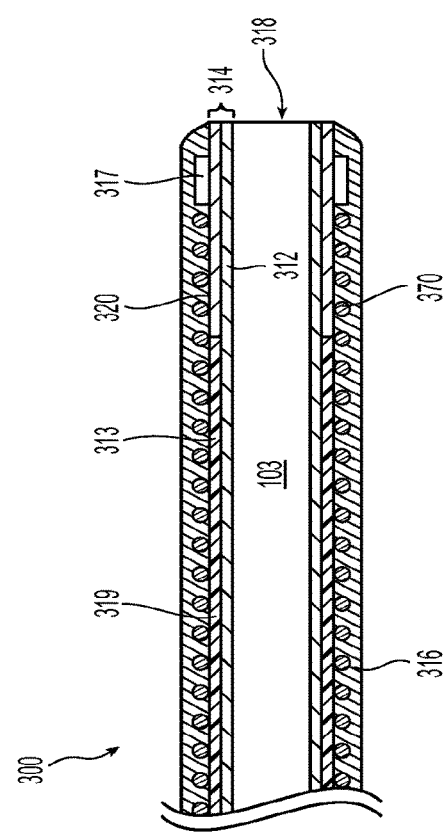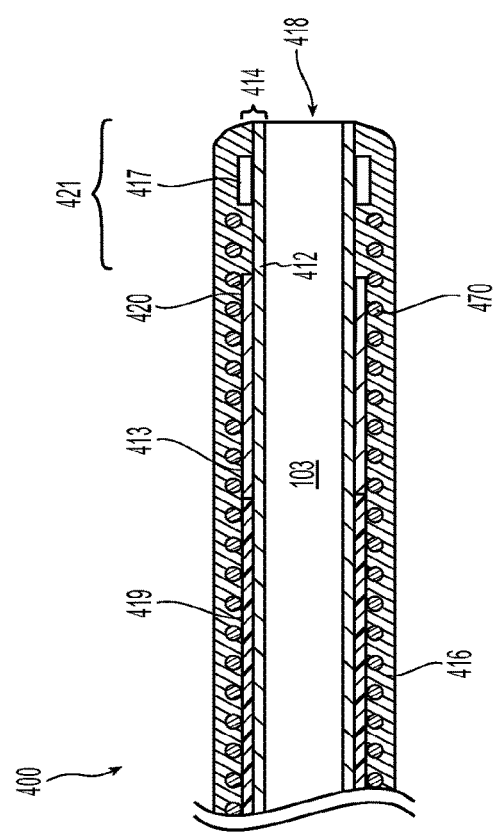

CATHETER SHAFT AND ASSOCIATED DEVICES, SYSTEMS, AND METHODS

This application is a continuation of U.S. patent application Ser. No. 14/852,268, filed Sep. 11, 2015, the entire content of which is incorporated by reference herein.

TECHNICAL FIELD

The present technology relates generally to catheters. More specifically, the invention relates to catheter shaft construction.

BACKGROUND

A wide variety of medical devices have been developed for intravascular use. Catheters, for example, are commonly used to facilitate navigation through and/or treatment within the anatomy of a patient. To direct the distal portion of the catheter to the correct location in the vasculature, a physician must apply longitudinal forces, and sometimes rotational forces (i.e., torsional forces), from the proximal end of the catheter. For the catheter shaft to transmit these forces from the proximal end to the distal end, the catheter must be sufficiently rigid to be pushed through the blood vessel (a property commonly referred to as "pushability"), yet flexible enough to navigate through the often tortuous bends in the blood vessel. The catheter may also require sufficient torsional stiffness to transmit the applied torque (a property commonly referred to as "torqueability"). A need exists for catheter shafts that accomplish a balance between longitudinal rigidity, torsional stiffness, and flexibility.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 1A is a side view of a catheter in accordance with the present technology.

FIG. 1B is a cross-sectional side view of a portion the catheter shaft shown in FIG. 1A.

FIG. 3 is a cross-sectional side view of a distal portion of an elongated catheter shaft configured in accordance with the present technology.

FIG. 4 is a cross-sectional side view of a distal portion of an elongated catheter shaft configured in accordance with the present technology.

DETAILED DESCRIPTION

Figure 2:
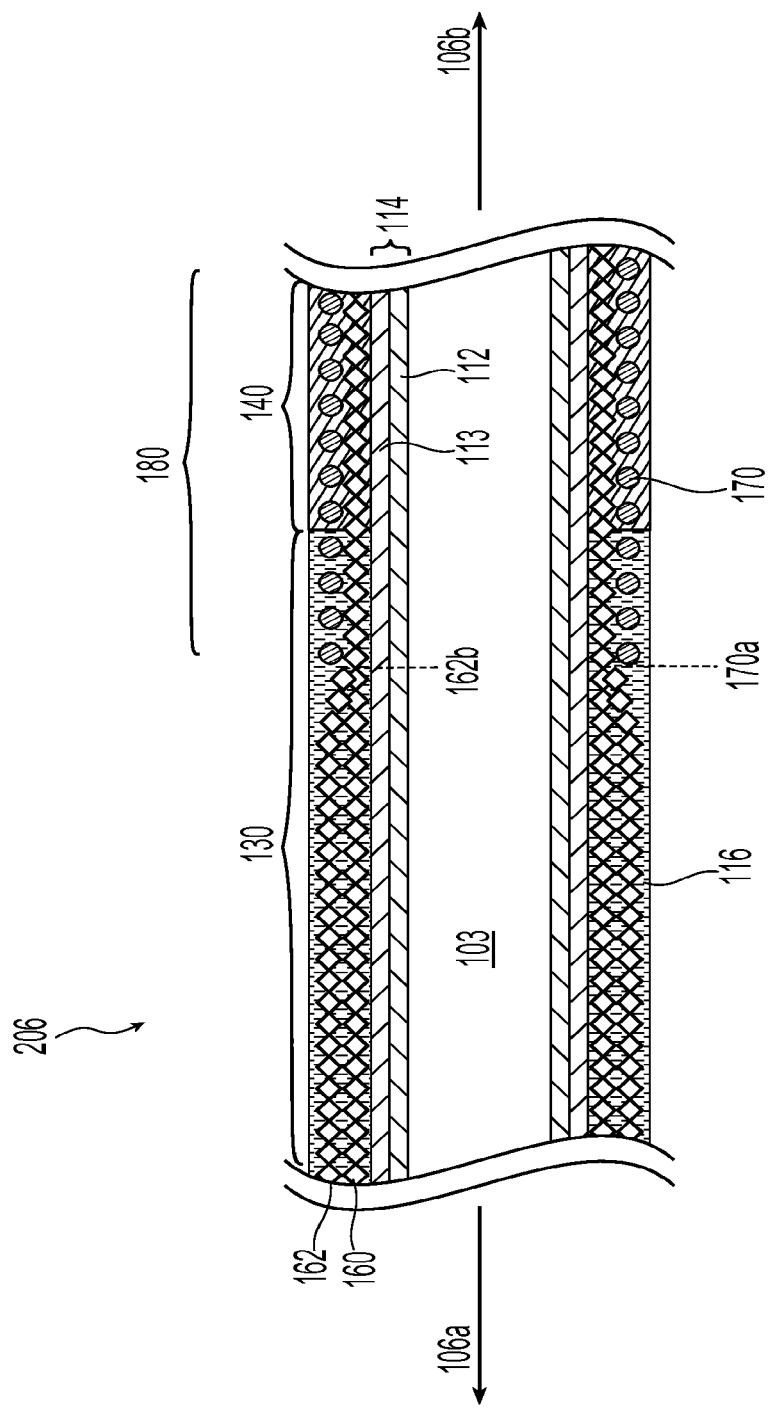
FIG. 2 is a cross-sectional side view of a portion of an elongated catheter shaft configured in accordance with another embodiment of the present technology.

The present technology is directed to catheters and associated methods of manufacture. Specific details of several embodiments of catheter devices, systems, and methods in accordance with the present technology are described below with reference to FIGS. 1A-8. With regard to the terms "distal" and "proximal" within this description, unless otherwise specified, the terms can reference a relative position of the portions of a catheter and/or an associated device with reference to an operator and/or a location in the vasculature. Also, the term "thickness" as used herein with respect to a particular material or layer refers to the perpendicular distance between the plane running through and generally parallel with the radially outermost surface of the particular material or layer and the plane running through and generally parallel with the radially innermost surface of the particular material or layer.

I. SELECTED EMBODIMENTS OF CATHETER SHAFTS OF THE PRESENT TECHNOLOGY

FIG. 1A is a side view of a catheter 100 configured in accordance with an embodiment of the present technology, and FIG. 1B is a cross-sectional side view of a portion of the catheter 100 shown in FIG. 1A. Referring to FIGS. 1A-1B together, the catheter 100 includes a handle assembly 101 and an elongated shaft 106 having a proximal portion 106a coupled to the handle assembly 101 and a distal portion 106b. The handle assembly 101 includes a hub 102 configured to facilitate connection to other devices (e.g., a syringe, a Y-adapter, etc.) and a transition portion 104 configured to provide strain relief at the proximal portion 106a. In other embodiments, the handle assembly 101 can have other suitable configurations based on the desired functions and characteristics of the catheter 100.

The shaft 106 is a generally tubular member having an inner surface that defines a lumen 103 (FIG. 1B) extending from the proximal portion 106a of the shaft 106 to an opening 118 at the distal terminus of the distal portion 106b. In some embodiments, the shaft 106 can include a radiopaque marker 117 (FIG. 1B) surrounding the lumen 103 at or just proximal to the opening 118. The lumen 103 is configured to slidably receive and facilitate the passage therethrough of one or more medical devices, such as guidewires, balloon catheters, implants, intrasaccular occlusion devices (e.g., coils, expandable cages, expandable meshes, etc.), infusion devices, stents and/or stent-grafts, intravascular occlusion devices, clot retrievers, implantable heart valves, and other suitable medical devices and/or associated delivery systems. Additionally, the lumen 103 is configured to receive one or more fluids therethrough, such as radiopaque dye, saline, drugs, and the like.

The size of the lumen 103 can vary, depending on the desired characteristics of the catheter 100. For example, in some embodiments the shaft 106 can have an inner diameter (e.g., lumen diameter) between about 0.01 inches and about 0.05 inches (e.g., 0.017 inches, 0.0445 inches, etc.), and in some embodiments between about 0.02 inches and about 0.045 inches (e.g., 0.021 inches, etc.). In a particular embodiment, the inner diameter is between about 0.025 inches and about 0.04 inches (e.g., 0.027 inches, 0.032 inches, etc.). Although the shaft 106 shown in FIG. 1A has a generally round cross-sectional shape, it will be appreciated that the shaft 106 can include other cross-sectional shapes or combinations of shapes. For example, the cross-sectional shape of the shaft 106 can be oval, rectangular, square, triangular, polygonal, and/or any other suitable shape and/or combination of shapes.

The outer diameter of the shaft 106 can be the same or vary along its length. For example, in the embodiment shown in FIGS. 1A-1B, the shaft 106 has a first portion 190 with a first diameter, a tapered portion 192 with a diameter that decreases in a proximal to distal direction, and a second portion 194 with a second diameter less than the first diameter. The length of the tapered portion 192 can be between about 1 cm and about 5 cm. In some embodiments, the shaft 106 does not include a second portion 194 and the tapered portion 192 extends distally to the distal terminus of the shaft 106. In other embodiments, the shaft 106 has an outer diameter that is generally constant along its length. Moreover, the length and/or outside diameter of the shaft 106 is generally selected for the desired use of the catheter 100. For example, in those embodiments where the catheter 100 is configured as a guide catheter for enabling intravascular insertion and navigation, the outside diameter of the shaft 106 can be between about 3 Fr and about 10 Fr. In those embodiments where the catheter 100 is configured as a microcatheter for use within small anatomies of the patient, the outside diameter of the shaft 106 can be between about 1 Fr and about 3 Fr.

Many embodiments of the present technology are particularly useful in treating targets located in tortuous and narrow vessels, such as certain sites in the neurovascular system, the coronary vascular system, or the peripheral vascular system (e.g., the superficial femoral, popliteal, or renal arteries). Neurovascular target sites, such as sites in the brain, are often accessible only via a tortuous vascular path. Although some embodiments of the catheter 100 are described in terms of intravascular use, in other embodiments the catheter 100 may be suited for uses in the digestive system, soft tissues, and/or any other insertion into an organism for medical uses. For example, in some embodiments, the catheter 100 may be significantly shorter and used as an introducer sheath, while in other embodiments the catheter 100 may be adapted for other medical procedures.

In the embodiment shown in FIG. 1B, the elongated shaft 106 includes an inner polymer structure 114 and an outer polymer structure 116 surrounding at least a portion of the inner polymer structure 114. The shaft 106 shown in FIG. 1B also has an inner braid 160 embedded in the outer polymer structure 116, an outer braid 162 surrounding at least a portion of the inner braid 160, and a coil 170 wrapped around at least a portion of the inner polymer structure 114. Each of these subcomponents will now be described in greater detail.

Referring again to FIGS. 1A-1B together, the inner polymer structure 114 extends from the proximal portion 106a of the shaft 106 to a location within the distal portion 106b of the shaft 106. For example, in the embodiment shown in FIG. 1B, the inner polymer structure 114 extends from the proximal portion 106a of the shaft 106 to the opening 118 at the distal terminus of the distal portion 106b (e.g., the entire length of the shaft 106 or substantially the entire length of the shaft 106). In other embodiments, the inner polymer structure 114 extends along only a portion of the length of the shaft 106 and/or has a proximal and/or a distal terminus that does not correspond to a proximal terminus and/or a distal terminus, respectively, of the shaft 106. The length of the inner polymer structure 114 can vary depending upon, for example, the length of the shaft 106 and the desired characteristics and functions of the catheter 100.

The inner polymer structure 114 can be made of any suitable polymer (and/or combination of multiples polymers) and by any suitable process. Suitable polymers can include, for example, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PFA), polyether-ester, platinum, polymer/metal composites, etc., or mixtures, blends or combinations thereof, and may also include or be made up of a lubricious polymer having a low coefficient of friction. In some embodiments (not shown), the inner polymer structure 114 includes one or more metals or metal alloys and/or combinations thereof. In a particular embodiment, the inner polymer structure 114 does not include any polymer material and solely comprises a metal and/or metal alloy.

The inner polymer structure 114 can include a single layer of material or it can have two or more layers of the same or different materials. For example, in the embodiment shown in FIG. 1B, the inner polymer structure 114 includes a first layer 112 and a second layer 113 surrounding at least a portion of the first layer 112. An inner surface of the first layer 112 defines the shaft lumen 103. The first layer 112 can comprise a lubricious polymer such as HDPE or PTFE, for example, or platinum, PEEK, PE, PP, or a copolymer of tetrafluoroethylene, such as FEP, a copolymer of tetrafluoroethylene with perfluoroethers, such as perfluoroalkoxy alkanes (PFA) (more specifically, perfluoropropyl vinyl ether or perfluoromethyl vinyl ether), or the like. The second layer 113 can be made of any of the materials described above with respect to the inner polymer structure 114 such as, for example, PEBA, PVC, PE, etc. In other embodiments, the inner polymer structure 114 can be formed of a single layer (e.g., only the first layer 112, only the second layer 113, etc.), and in other embodiments the inner polymer structure 114 can include more than two layers (e.g., three layers, four layers, etc.) depending upon the desired characteristics of the catheter 100. In some embodiments the first and second layers 112, 113 have generally the same lengths and are coextensive along the length of the shaft 106, and in other embodiments the first and second layers 112, 113 have different lengths and/or are not coextensive along the shaft 106. For example, in a particular embodiment, the second layer 113 extends along only a portion of the length of the shaft 106 while the first layer 112 extends the entire length (or substantially the entire length) of the shaft 106. In any of the above embodiments, the first layer 112 can have a thickness of about 0.0005 inches to about 0.005 inches, or about 0.001 inches to about 0.003 inches. Also, in any of the above embodiments, the second layer 113 can have a thickness of about 0.0005 inches to about 0.005 inches, or about 0.001 inches to about 0.003 inches.

The stiffness of the inner polymer structure 114 can be generally uniform along its length, or the stiffness can vary along its length. The stiffness variation is a function of the size, shape, thickness, and/or materials of the inner polymer structure 114. In embodiments where the stiffness of the inner polymer structure 114 varies along its length, the stiffness can change continuously (e.g., gradually) and/or be stepped from one section to another. In some embodiments, the stiffness of the inner polymer structure 114 decreases in a proximal to distal direction along its length. In other embodiments, the stiffness of the inner polymer structure 114 increases in a proximal to distal direction along it length, and/or increases and decreases in a proximal to distal direction along its length. Additionally, the inner polymer structure 114 can be made of or include a radiopaque material for radiographic visualization. Exemplary radiopaque materials include, for example, gold, platinum, palladium, tantalum, tungsten alloy, polymer materials loaded with radiopaque fillers, and the like. Likewise, in some embodiments, the inner polymer structure 114 is made of or include a material that may aid in MRI imaging, such as, for example, tungsten, Elgiloy, MP35N, nitinol, and others.

In the embodiment shown in FIGS. 1A-1B, the outer polymer structure 116 directly contacts at least a portion of the inner polymer structure 114 and encases at least a portion of each of the inner braid 160, the outer braid 162, and the coil 170. The outer polymer structure 116 extends distally from the proximal portion 106a of the shaft 106 to a location within the distal portion 106b of the shaft 106 (e.g., the entire length of the shaft 106 or substantially the entire length of the shaft 106). The length of the outer polymer structure 116 can vary depending upon, for example, the length of the shaft 106 and the desired characteristics and functions of the catheter 100. In some embodiments, the outer polymer structure 116 extends substantially the entire length of the shaft 106. In other embodiments, the outer polymer structure 116 extends along only a portion of the length of the shaft 106 and/or has a proximal and/or distal terminus that does not correspond to a proximal terminus and/or distal terminus, respectively, of the shaft 106.

The outer polymer structure 116 (and/or portions thereof) can be made of any suitable polymer (or composites or combinations thereof) and by any suitable process. Suitable polymers can include, for example, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PFA), polyether-ester, platinum, polymer/metal composites, etc., or mixtures, blends or combinations thereof. In several embodiments, the outer polymer structure 116 is or at least includes a lubricious polymer. In some embodiments (not shown), the outer polymer structure 116 includes one or more metals or metal alloys (combinations thereof). In a particular embodiment, the outer polymer structure 116 does not include any polymer material and solely comprises a metal and/or metal alloy.

In some embodiments, the stiffness of the outer polymer structure 116 varies along its length. In such embodiments, the stiffness variation may be continuous or stepped by varying the size, shape, thickness, and/or material composition of the outer polymer structure 116. For example, in the embodiment shown in FIGS. 1A-1B, the outer polymer structure 116 includes four unique portions along its length (labeled proximal to distal as first, second, third and fourth portions 120, 130, 140, and 150, respectively) in which the respective stiffnesses of the portions 120, 130, 140, 150 decrease sequentially in a proximal to distal direction. For example, the first portion 120 has a first stiffness, the second portion 130 has a second stiffness less than the first stiffness, the third portion 140 has a third stiffness less than the second stiffness, and the fourth portion 150 has a fourth stiffness less than the third stiffness. In other embodiments, the stiffness of the outer polymer structure 116 and/or the stiffnesses of the individual portions 120, 130, 140, 150 can increase in a proximal to distal direction (e.g., the second portion 130 can be stiffer than the first portion 120, etc.), increase and decrease in a proximal to distal direction (e.g., the second portion 130 can be stiffer than the first portion 120 but less stiff than the third portion 140, etc.), or be generally uniform in a proximal to distal direction. In other embodiments, the outer polymer structure 116 can have more or fewer portions (e.g., one continuous portion, two portions, three portions, five portions, etc.).

In some embodiments, one or both of the first and second portions 120, 130 can have an individual thickness of about 0.003 inches to about 0.005 inches, and in some embodiments, about 0.004 inches to about 0.010 inches. The fourth portion 150 can have a thickness of about 0.001 inches to about 0.003 inches. The proximal portion of the tapered portion 192 can have a thickness equivalent to that of the corresponding second portion 130, and the distal portion of the tapered portion 192 can have a thickness generally equivalent to that of the corresponding fourth portion 150. Thus, the third portion 140 can have a proximal thickness between about 0.003 inches to about 0.005 inches, or in some embodiments about 0.004 inches to about 0.010 inches, and a distal portion have a thickness of about 0.001 inches to about 0.003 inches.

The portions 120, 130, 140, 150, either individually or any combination thereof, can be made of the same or different materials, have the same or different size, have the same or different thickness, and/or have the same or different cross-sectional shape. In some embodiments, the outer polymer structure 116 can include two or more layers (e.g., an inner layer surrounding an outer layer, etc.), and each layer can have the same or different material compositions, thicknesses, and/or stiffnesses. Additionally, the portions 120, 130, 140, 150, either individually or any combination thereof, can have a uniform or varying stiffness along its respective length. In other words, the portions 120, 130, 140, 150, either individually or any combination thereof, can have a uniform or varying size, shape, thickness, and/or material composition along its respective length. For example, in the embodiment shown in FIG. 1B, each of the portions 120, 130, 140, 150 has a constant material composition and cross-sectional shape along its respective length. Each of the first, second, and fourth portions 120, 130, 150 also has a generally constant thickness along its respective length; accordingly, each of the first, second, and fourth portions 120, 130, 150 has a generally constant stiffness along its respective length. The third portion 140, however, includes the tapered portion 192 (FIG. 1A) and thus varies in thickness (and stiffness) along its length. In other embodiments, the third portion 140 does not coincide with the tapered portion 192 and/or the tapered portion 192 spans more than one of the portions 120, 130, 140, 150.

It will be appreciated that while the inner polymer structure 114 and the outer polymer structure 116 are described herein as separate components with respect to the illustrated embodiments, the inner and outer polymer structures 114, 116 can be provided as a single layer or structure. For example, the inner polymer structure 114 and outer polymer structure 116 may be provided separately, but attached or combined together to physically form a single layer (e.g., a single homogeneous material).

Referring still to the embodiment shown in FIG. 1B, the inner braid 160 is on and around the inner polymer structure 114, and the outer polymer structure 116 is on and around the inner braid 160. In some embodiments, the inner braid 160 directly contacts at least a portion of both the inner polymer structure 114 and the outer polymer structure 116. In other embodiments, the outer polymer structure 116 is between at least a portion of the inner polymer structure 114 and at least a portion of the inner braid 160. In the embodiment shown in FIGS. 1A-1B, the inner braid 160 extends distally from the proximal portion 106a of the shaft 106 to a distal terminus 160b aligned with or just proximal of the distal terminus of the shaft 106. In other embodiments, the inner braid 160 extends the entire length of the shaft 106. The length of the inner braid 160 can vary depending upon, for example, the length of the shaft 106 and the desired characteristics and functions of the catheter 100.

In some embodiments, at least a portion of the inner braid 160 is coextensive with at least a portion of the outer braid 162. For example, in the embodiment shown in FIG. 1B, the inner braid 160 has a distal terminus 160b located at a position along the shaft 106 distal of a proximal terminus (not shown) of the outer braid 162 and proximal of a distal terminus 162b of the outer braid 162. In other embodiments (not shown), no portion of the inner braid 160 is coextensive with a portion of the outer braid 162. Additionally, in some embodiments at least a portion of the inner braid 160 is coextensive with at least a portion of the coil 170, and in other embodiments the inner braid 160 is adjacent to and/or spaced apart from the coil 170 along the length of the shaft 106. For example, in the embodiment shown in FIG. 1B, the distal terminus 160b of the inner braid 160 is located at a position along the shaft 106 proximal of a proximal terminus 170a of the coil 170 such that no portion of the inner braid 160 is coextensive with any portion of the coil 170. Alternatively, in some embodiments (not shown) the distal terminus 160b of the inner braid 160 is located at a position along the shaft 106 distal of a proximal terminus 170a of the coil 170 such that at least a portion of the inner braid 160 is coextensive with at least a portion of the coil 170.

In the embodiment shown in FIGS. 1A-1B, the outer braid 162 is around the inner braid 160, and the outer polymer structure 116 contacts the outer braid 162. In some embodiments the outer braid 162 directly contacts the inner braid 160. In other embodiments, the outer polymer structure 116 is between at least a portion of the inner braid 160 and at least a portion of the outer braid 162. In the embodiment shown in FIG. 1B, a distal portion of the outer braid 162 is around a proximal portion of the coil 170. In some embodiments the outer braid 162 directly contacts the coil 170. In other embodiments, the outer polymer structure 116 is between at least a portion of the outer braid 162 and at least a portion of the coil 170.

The outer braid 162 extends distally from the proximal portion 106a of the shaft 106 to a distal terminus 162b proximal to the distal terminus of the shaft 106. In other embodiments, the outer braid 162 extends the entire length of the shaft 106. The length of the outer braid 162 can vary depending upon, for example, the length of the shaft 106 and the desired characteristics and functions of the catheter 100. In some embodiments, at least a portion of the outer braid 162 is coextensive with at least a portion of the coil 170. For example, in the embodiment shown in FIG. 1B, the distal terminus 162b of the outer braid 162 is located at a position along the shaft 106 that is distal of the proximal terminus 170a of the coil 170. In those embodiments where at least a portion of the outer braid 162 is coextensive with at least a portion of the coil 170, the coextensive portions of the outer braid 162 and the coil 170 form an overlapping region 180. As shown in FIG. 1B, in some embodiments the outer braid 162 surrounds the coil 170 within the overlapping region 180. In other embodiments, the coil 170 surrounds the outer braid 162 within the overlapping region 180 (FIG. 2, described in greater detail below). In yet other embodiments, the outer braid 162 is spaced apart from and/or adjacent to the coil 170 such that no portion of the outer braid 162 is coextensive with any portion of the coil 170.

The inner braid 160 and/or the outer braid 162 can individually have a generally uniform pitch along its respective length or may have a varying pitch along its respective length. The flexibility of the individual inner braid 160 and/or the outer braid 162 may vary continuously along its respective length by continuously varying the pitch or may vary along its respective length in a stepwise fashion by stepwise varying the pitch. Moreover, the inner braid 160 and/or the outer braid 162 can individually have a generally constant braid angle along its respective length or have a varying braid angle along its respective length to provide different zones of stiffness and/or flexibility. The inner braid 160 and/or the outer braid 162 can be formed of braided filaments having the same or varying diameters (individually and/or relative to the other braid). In some embodiments, the inner braid 160 and/or the outer braid 162 are further shaped using a heat setting process. Additionally, the inner braid 160 and the outer braid 162 can have the same or different pitch, stiffness, braid angle, filament diameters, and filament count. In some embodiments, the inner and/or outer braids 160, 162 individually have a pitch of 45 PPI to 80 PPI. In a particular embodiment, the shaft 106 includes a single braid. Additionally, in some embodiments, the inner braid 160 and/or the outer braid 162 can be made of or include a radiopaque or imaging material.

The inner 160 and/or outer braids 162 are formed of a plurality of interwoven wires. The wires can have a circular or rectangular cross-sectional shape. The wires can be made of one or more metals, such as stainless steel, platinum, silver, tantalum, and the like. In some embodiments, the wires can include or be made of non-metallic materials. In some embodiments, the wires are made of a superelastic or shape-memory material, such as nitinol. For those embodiments utilizing wires having a rectangular shape, the wires can have a cross-sectional area of about 0.0005 inches by 0.0025 inches to about 0.001 inches by 0.005 inches.

The coil 170 can be one or more round wires or flat ribbons helically wound around the inner polymer structure 114. In the embodiment shown in FIGS. 1A-1B, the outer polymer structure 116 encases the coil 170. The proximal terminus 170a of the coil 170 is positioned along the distal portion 106b of the shaft 106, and the distal terminus 170b of the coil 170 is positioned generally in alignment with or just proximal to the distal terminus of the shaft 106. Accordingly, the coil 170 is completely disposed within the distal portion of the shaft. In other embodiments, at least a portion of the coil 170 is outside of the distal portion 106b of the shaft 106. The pitch of adjacent turns of the coil 170 may be tightly wound so that each turn touches the succeeding turn or the pitch may be set such that the coil 170 is wound in an open fashion. The pitch of the coil 170 can be the same or may vary along the length of the coil 170. The coil 170 can have a pitch of about 0.004 inches to about 0.014 inches. In some embodiments, the pitch of the coil 170 depends on the inner diameter of the shaft 106. For example, for a shaft inner diameter of about 0.017 inches, the coil 170 can have a pitch of about 0.004 inches to about 0.009 inches. For a shaft inner diameter of about 0.021 inches, the coil 170 can have a pitch of about 0.006 inches to about 0.011 inches. For a shaft inner diameter of about 0.027 inches, the coil 170 can have a pitch of about 0.007 inches to about 0.012 inches. For a shaft inner diameter of about 0.0045 inches, the coil 170 can have a pitch of about 0.010 inches to about 0.014 inches.

Additionally, in some embodiments, the coil 170 or portions thereof can be made of or include a radiopaque or imaging material.

The wire of the coil 170 can be made of one or more metals, such as stainless steel, platinum, silver, tantalum, and the like. In other embodiments, the wire of the coil 170 can include or be made of non-metallic materials. In a particular embodiment, the wires are made of a superelastic or shape-memory material, such as nitinol The wire can have an outer diameter of about 0.001 inches to about 0.005 inches, or in some embodiments about 0.001 inches to about 0.003 inches.

It will be appreciated that the inner braid 160, outer braid 162, and coil 170 can have other suitable configurations and/or relative positions along the length of the shaft 106. For example, in some embodiments the inner braid 160 can be coextensive with at least a portion of the coil 170, and in some embodiments the inner braid 160 can be generally coextensive with the outer braid 162. In a particular embodiment, at least a portion of the outer braid 162 is not coextensive with a portion of the coil 170.

FIG. 2 is a cross-sectional side view of a portion of a catheter shaft 206 configured in accordance with another embodiment of the present technology. The shaft 206 can be generally similar to the shaft 106 shown in FIGS. 1A-1B, except the coil 170 in the shaft 206 of FIG. 2 surrounds the outer braid 162 within the overlapping region 180.

II. SELECTED EMBODIMENTS OF DISTAL PORTIONS OF CATHETER SHAFTS OF THE PRESENT TECHNOLOGY

FIGS. 3-8 are cross-sectional side views of distal portions of catheter shafts configured in accordance with the present technology. Any of the distal portions (or aspects thereof) described below can be combined with any of the catheter shafts described above with reference to FIGS. 1A-2. As described in greater detail below, the distal portion embodiments of the present technology include regions of varying stiffness and/or preferential bending that provide improved bending/buckling at the distal portion when contacting the wall of tortuous vessels, thereby improving ease of navigation of the corresponding shaft and/or distal portion.

FIG. 3 is a cross-sectional side view of a distal portion 300 of a catheter shaft configured in accordance with the present technology. The distal portion 300 can include a radiopaque marker 317, an inner polymer structure 314, an outer polymer structure 316 surrounding at least a portion of the inner polymer structure 314, and a coil 370 wrapped around at least a portion of the inner polymer structure 314. As shown in FIG. 3, the inner polymer structure 314 extends the length of the distal portion 300 such that the inner polymer structure 314 terminates distally at an opening 318 at the distal terminus of the distal portion 300. The inner polymer structure 314 defines a lumen that can be generally continuous with the lumen 103 of any of the shaft embodiments described above with reference to FIGS. 1A-2.

The inner polymer structure 314 can include a single layer of material or it can have two or more layers of the same or different materials. For example, in the embodiment shown in FIG. 3, the inner polymer structure 314 includes a first layer 312 and a second layer 313 surrounding the first layer 312. Accordingly, an inner surface of the first layer 312 defines the shaft lumen 103 at the distal portion 300. The first layer 312 can comprise a lubricious polymer such as HDPE or PTFE, for example, or platinum, PEEK, PE, PP, or a copolymer of tetrafluoroethylene, such as FEP, a copolymer of tetrafluoroethylene with perfluoroethers, such as PFA (more specifically, perfluoropropyl vinyl ether or perfluoromethyl vinyl ether), or the like. The second layer 313 can be made of any of the materials described above with respect to the inner polymer structure 114. Moreover, in some embodiments the inner polymer structure 314 can be formed of a single layer (e.g., only the first layer 312, only the second layer 313, etc.), and in other embodiments the inner polymer structure 314 can include more than two layers (e.g., three layers, four layers) depending on the desired characteristics of the distal portion 300 of the catheter.

The stiffness of the inner polymer structure 314 can be generally uniform along its length, or the stiffness can vary along its length. In the embodiment shown in FIG. 3, the second layer 313 of the inner polymer structure 314 includes two unique portions along its length (labeled proximal to distal as first portion 319 and second portion 320). The first and second portions 319, 320 can have at least one of a different size, shape, thickness, and material composition such that the first portion 319 has a different stiffness than the second portion 320 (or in other words, the second portion 320 is softer than the first portion 319). For example, the first portion 319 can be a first material and the second portion 320 can be a second material different than the first material such that a stiffness of the first portion 319 is greater than a stiffness of the second portion 320. In other embodiments, a stiffness of the inner polymer structure 314 can increase in a proximal to distal direction along its length, or increase and decrease in a proximal to distal direction along its length. For example, in a particular embodiment, the second portion 320 can have a stiffness that is greater than or equal to the stiffness of the first portion 319. In other embodiments, the inner polymer structure 314 can have more or fewer portions (e.g., one continuous portion, three portions, four portions, etc.).

In the embodiment shown in FIG. 3, both the first and second layers 312, 313 of the inner polymer structure 314 extend along the entire length of the distal portion 300 such that the distal termini of both the first and second layers 312, 313 are at the distal terminus of the distal portion 300. Additionally, the second portion 319 of the second layer 313 defines a portion of the distal terminus of the distal portion 300 of the shaft. As such, the distal-most surfaces of both the inner and the outer polymer structures 314, 316 define the distal terminus of the distal portion 300 of the shaft. In other embodiments, the first layer 312 terminates proximal to the distal terminus of the distal portion 300.

Although the inner polymer structure 314 is shown having two portions 319, 320 in FIG. 3, in other embodiments the inner polymer structure 314 can have a single continuous portion or more than two portions (e.g., three portions, four portions, etc.). Moreover, although the second layer 313 is shown having multiple portions, in other embodiments the first layer 312 can additionally or alternatively include multiple portions.

Referring still to the embodiment shown in FIG. 3, the outer polymer structure 316 directly contacts at least a portion of the inner polymer structure 314 and encases at least a portion of the coil 370. For example, in the embodiment shown in FIG. 3, at least a portion of the surface of the coil 370 directly contacts the first and second portions 319, 320 of the second layer 313 of the inner polymer structure 314, while a remaining portion of the coil's surface directly contacts the outer polymer structure 316. Additionally, the outer polymer structure 316 extends along the length of the distal portion 300 such that a distal terminus of the outer polymer structure 316 corresponds to the distal terminus of the distal portion 300. In other embodiments, the outer polymer structure 316 extends along only a portion of the length of the distal portion 300 and/or has a proximal and/or distal terminus that does not correspond to a proximal terminus and/or distal terminus, respectively, of the distal portion 300. Moreover, the outer polymer structure 316 (and/or portions thereof) can be made of any of the materials described above with respect to the outer polymer structure 116.

The coil 370 can be one or more round wires or flat ribbons helically wound around the inner polymer structure 314, and the outer polymer structure 316 can encase at least a portion of the coil 370. The coil 370 can extend all or a portion of the length of the distal portion 300. For example, in the embodiment shown in FIG. 3, the coil 370 has a distal terminus that is aligned with or just proximal of the radiopaque marker 317, and the radiopaque marker 317 is proximal of the distal terminus of the distal portion 300. As such, a distal terminus of the coil 370 is spaced apart from a distal terminus of the shaft. The pitch of adjacent turns of the coil 370 may be tightly wound so that each turn touches the succeeding turn or the pitch may be set such that the coil 370 is wound in an open fashion. The pitch of the coil 370 can be the same or vary along the length of the coil 370. Additionally, in some embodiments, the coil 370 or portions thereof can be made of or include a radiopaque or imaging material.

FIG. 4 is a cross-sectional side view of a distal portion 400 of a catheter shaft configured in accordance with another embodiment of the present technology. The distal portion 400 can include a radiopaque marker 417, an inner polymer structure 414, an outer polymer structure 416 surrounding at least a portion of the inner polymer structure 414, and a coil 470 wound around at least a portion of the inner polymer structure 414. The inner polymer structure 414 defines a lumen that can be generally continuous with the lumen 103 of any of the shaft embodiments described above with reference to FIGS. 1A-2.

The inner polymer structure 414 can include a single layer of material or it can have two or more layers of the same or different materials. For example, in the embodiment in FIG. 4, the inner polymer structure 414 includes a first layer 412 and a second layer 413 surrounding the first layer 412. Accordingly, an inner surface of the first layer 412 defines the shaft lumen 103 at the distal portion 400. The first layer 412 can comprise a lubricious polymer such as HDPE or PTFE, for example, or platinum, PEEK, PE, PP, or a copolymer of tetrafluoroethylene, such as FEP, a copolymer of tetrafluoroethylene with perfluoroethers, such as PFA (more specifically, perfluoropropyl vinyl ether or perfluoromethyl vinyl ether), or the like. The second layer 413 can be made of any of the materials described above with respect to the inner polymer structure 414. Moreover, in some embodiments the inner polymer structure 414 can be formed of a single layer (e.g., only the first layer 412, only the second layer 413, etc.), and in other embodiments the inner polymer structure 414 can include more than two layers (e.g., three layers, four layers) depending upon the desired characteristics of the catheter.

The stiffness of the inner polymer structure 414 can be generally uniform along its length, or the stiffness can vary along its length. In the embodiment shown in FIG. 4, the second layer 413 of the inner polymer structure 414 includes two unique portions (labeled proximal to distal as first portion 419 and second portion 420) adjacent one another along its length having different stiffnesses. The first and second portions 419, 420 can have at least one of a different size, shape, thickness, and material composition such that the first portion 419 has a different stiffness than the second portion 420. For example, the first portion 419 can be a first material and the second portion 420 can be a second material different than the first material such that a stiffness of the first portion 419 is greater than a stiffness of the second portion 420. In other embodiments, a stiffness of the inner polymer structure 414 can increase in a proximal to distal direction along its length, or increase and decrease in a proximal to distal direction along its length. For example, in a particular embodiment, the second portion 420 has a stiffness that is greater than or equal to the stiffness of the first portion 419.

In the embodiment shown in FIG. 4, the second layer 413 of the inner polymer structure 414 extends along only a portion of the length of the distal portion 400 such that a distal terminus of the second layer 413 is proximal of the distal terminus of the outer polymer structure 416 and the distal terminus of the distal portion 400. Accordingly, in contrast to the embodiment shown in FIG. 3, only the distal-most portions of the outer polymer structure 416 and the first layer 312 define the distal terminus of the distal portion 400 of the shaft (and not the second layer 313). Likewise, a distal region 421 of the distal portion 400 does not include the second layer 413 and comprises only the first layer 412, the outer polymer structure 416, the radiopaque marker 417, and a portion of the coil 470. Accordingly, the distal region 421 is more flexible than the remainder of the distal portion 400. In some embodiments, the first layer 412 and/or the coil 470 terminates proximal of the distal region 421 such that the distal region 412 comprises the first layer 412 and the outer polymer structure 416. The length of the distal region 421 can be between about 0.5 mm and about 5 cm.

Although the inner polymer structure 414 is shown having two portions 419, 420 in FIG. 4, in other embodiments the inner polymer structure 414 can have a single continuous portion or more than two portions (e.g., three portions, four portions, etc.). Moreover, although the second layer 413 is shown having multiple portions, in other embodiments the first layer 412 can additionally or alternatively include multiple portions.

Referring still to the embodiment shown in FIG. 4, the outer polymer structure 416 directly contacts at least a portion of the inner polymer structure 414 and encases at least a portion of the coil 470. For example, in the embodiment shown in FIG. 4, at least a portion of the surface of the coil 470 directly contacts the inner polymer structure 414, while a remaining portion of the coil's surface directly contacts the outer polymer structure 416. As shown in FIG. 4, in some embodiments the outer polymer structure 416 extends along the length of the distal portion 400 such that a distal terminus of the outer polymer structure 416 corresponds to the distal terminus of the distal portion 400. The outer polymer structure 416 (and/or portions thereof) can be made of any of the materials described above with respect to the outer polymer structure 116.

The coil 470 can be one or more round wires or flat ribbons helically wound around the inner polymer structure 414. The coil 470 can extend all or a portion of the length of the distal portion 400. For example, in the embodiment shown in FIG. 4, the coil 470 has a distal terminus that is aligned with or just proximal of the radiopaque marker 417, and the radiopaque marker 417 is proximal of the distal terminus of the distal portion 400. The pitch of adjacent turns of the coil 470 may be tightly wound so that each turn touches the succeeding turn or the pitch may be set such that the coil 470 is wound in an open fashion. The pitch of the coil 470 can be the same or vary along the length of the coil 470. Additionally, in some embodiments, the coil 470 or portions thereof can be made of or include a radiopaque or imaging material.

The distal portions 300/400 provide several advantages over distal portions of conventional catheters, especially microcatheters for delivering occlusive devices (such as coils) to cerebral aneurysms. For example, the distal portions 300 and 400 have a (relatively) softer distal tip and a (relatively) stiffer region immediately adjacent and proximal to the softer distal tip. Such a construction allows for improved bending and trackability at the distal tip bend (for positioning at the aneurysm neck) while the proximal stiffer region of the distal portion 300/400 provides additional support and stability to the distal portion 300/400, thereby lessening or preventing kickback of the shaft during deployment of an occlusive device (such as a coil) in an aneurysm.

Figure 5:
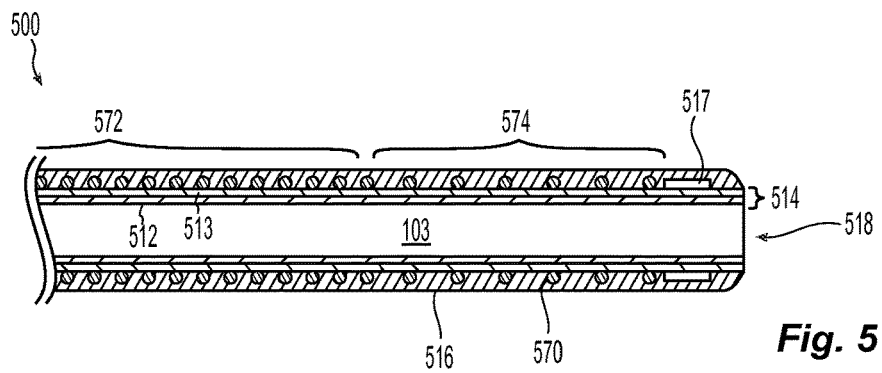
FIG. 5 is a cross-sectional side view of a distal portion of an elongated catheter shaft configured in accordance with the present technology.

FIG. 5 is a cross-sectional side view of a distal portion 500 of a catheter shaft configured in accordance with another embodiments of the present technology. The distal portion 500 can include a radiopaque marker 517, an inner polymer structure 514, an outer polymer structure 516 surrounding at least a portion of the inner polymer structure 514, and a coil 570 wound around at least a portion of the inner polymer structure 514. In the embodiment shown in FIG. 5, the inner polymer structure 514 extends the length of the distal portion 500 such that the inner polymer structure 514 terminates distally at an opening 518 at the distal terminus of the distal portion 500. The inner polymer structure 514 defines a lumen that can be generally continuous with the lumen 103 of any of the shaft embodiments described above with reference to FIGS. 1A-2.

The inner polymer structure 514 can include a single layer of material or it can have two or more layers of the same or different materials. For example, in the embodiment shown in FIG. 5, the inner polymer structure 514 includes a first layer 512 and a second layer 513 surrounding the first layer 512. As such, an inner surface of the first layer 512 defines the shaft lumen 103. The second layer 513 can be made of any of the materials described above with respect to the inner polymer structure 514. The first layer 512 can comprise a lubricious polymer such as HDPE or PTFE, for example, or platinum, PEEK, PE, PP, or a copolymer of tetrafluoroethylene, such as FEP, a copolymer of tetrafluoroethylene with perfluoroethers, such as PFA (more specifically, perfluoropropyl vinyl ether or perfluoromethyl vinyl ether), or the like. Moreover, in some embodiments the inner polymer structure 514 can be formed of a single layer (e.g., only the first layer 512, only the second layer 513, etc.), and in other embodiments the inner polymer structure 514 can include more than two layers (e.g., three layers, four layers) depending upon the desired characteristics of the device.

The outer polymer structure 516 directly contacts at least a portion of the inner polymer structure 514 and encases at least a portion of the coil 570. For example, in the embodiment shown in FIG. 5, at least a portion of the surface of the coil 570 directly contacts the second layer 513 of the inner polymer structure 514, while a remaining portion of the coil's surface directly contacts the outer polymer structure 516. As shown in FIG. 5, in some embodiments the outer polymer structure 516 extends along the length of the distal portion 500 such that a distal terminus of the outer polymer structure 516 corresponds to the distal terminus of the distal portion 500. The outer polymer structure 516 (and/or portions thereof) can be made of any of the materials described above with respect to the outer polymer structure 116.

The coil 570 can be one or more round wires or flat ribbons helically wound around the inner polymer structure 514. The coil 570 can extend all or a portion of the length of the distal portion 500. For example, in the embodiment shown in FIG. 5, the coil 570 has a distal terminus that is aligned with or just proximal of the radiopaque marker 517, and the radiopaque marker 517 is proximal of the distal terminus of the distal portion 500. The pitch of adjacent turns of the coil 570 may be tightly wound so that each turn touches the succeeding turn or the pitch may be set such that the coil 570 is wound in an open fashion. The pitch of the coil 570 can be the same or vary along the length of the coil 570. For example, in the embodiment shown in FIG. 5, the coil 570 has a first portion 572 and a second portion 574 distal of the first portion 572. The first portion 572 has a first pitch and the second portion 574 has a second pitch that is greater than the first pitch. Accordingly, a length of the distal portion 500 corresponding to the first portion 572 of the coil 570 is less flexible than a length of the distal portion 500 corresponding to the second portion 574 of the coil 570. Additionally, in some embodiments, the coil 570 or portions thereof can be made of or include a radiopaque or imaging material.

Figure 6:
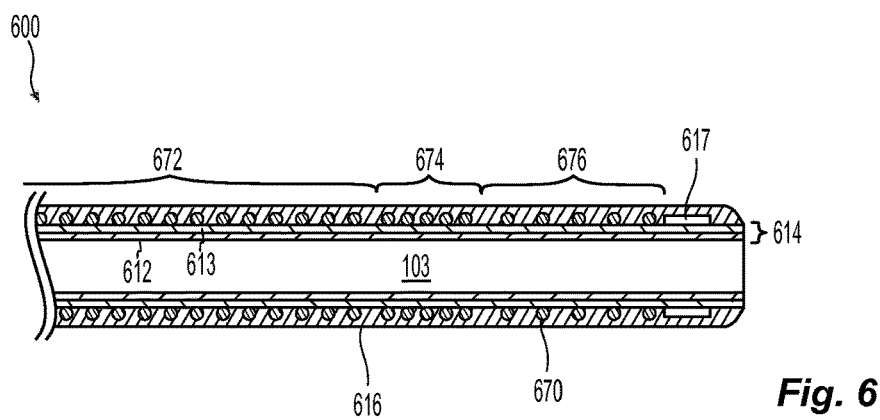
FIG. 6 is a cross-sectional side view of a distal portion of an elongated shaft configured in accordance with the present technology.

FIG. 6 is a cross-sectional side view of a distal portion 600 of a catheter shaft configured in accordance with the present technology. The distal portion 600 can include a radiopaque marker 617, an inner polymer structure 614, an outer polymer structure 616 surrounding at least a portion of the inner polymer structure 614, and a coil 670 wound around at least a portion of the inner polymer structure 614. In the embodiment shown in FIG. 6, the inner polymer structure 614 extends the length of the distal portion 600 such that the inner polymer structure 614 terminates distally at an opening 618 at the distal terminus of the distal portion 600. The inner polymer structure 614 defines a lumen that can be generally continuous with the lumen 103 of any of the shaft embodiments described above with reference to FIGS. 1A-2.

The inner polymer structure 614 can include a single layer of material or it can have two or more layers of the same or different materials. For example, as shown in FIG. 6, the inner polymer structure 614 can include a first layer 612 and a second layer 613 surrounding the first layer 612. As such, an inner surface of the first layer 612 defines the shaft lumen 103. The second layer 613 can be made of any of the materials described above with respect to the inner polymer structure 614. The first layer 612 can include a lubricious polymer such as HDPE or PTFE, for example, or a copolymer of tetrafluoroethylene with perfluoroalkyl vinyl ether (PFA) (more specifically, perfluoropropyl vinyl ether or perfluoromethyl vinyl ether), or the like. Moreover, in some embodiments the inner polymer structure 614 can be formed of a single layer (e.g., only the first layer 612, only the second layer 613, etc.), and in other embodiments the inner polymer structure 614 can include more than two layers (e.g., three layers, four layers) depending upon the desired characteristics of the device.

The outer polymer structure 616 directly contacts at least a portion of the inner polymer structure 614 and encases at least a portion of the coil 670. For example, in the embodiment shown in FIG. 6, at least a portion of the surface of the coil 670 directly contacts the second layer 613 of the inner polymer structure 614, while a remaining portion of the coil's surface directly contacts the outer polymer structure 616. In some embodiments the outer polymer structure 616 extends along the length of the distal portion 600 such that a distal terminus of the outer polymer structure 616 corresponds to the distal terminus of the distal portion 600. The outer polymer structure 616 (and/or portions thereof) can be made of any of the materials described above with respect to the outer polymer structure 116.

The coil 670 can be one or more round wires or flat ribbons helically wound around the inner polymer structure 614. The coil 670 can extend all or a portion of the length of the distal portion 600. For example, in the embodiment shown in FIG. 6, the coil 670 has a distal terminus that is aligned with or just proximal of the radiopaque marker 617, and the radiopaque marker 617 is proximal of the distal terminus of the distal portion 600. The pitch of adjacent turns of the coil 670 may be tightly wound so that each turn touches the succeeding turn or the pitch may be set such that the coil 670 is wound in an open fashion. The pitch of the coil 670 can be the same or vary along the length of the coil 670. For example, in the embodiment shown in FIG. 6, the coil 670 has a first portion 672, a second portion 674 distal of the first portion 672, and a third portion 676 distal of the second portion 674. The first portion 672 has a first pitch, the second portion 674 has a second pitch less than the first pitch, and the third portion 676 has a third pitch greater than the second pitch. Accordingly, regions of the distal portion 600 corresponding to the first and third portions 672, 676 of the coil 670 are more flexible than a region of the distal portion 600 corresponding to the second portion 674 of the coil 670. In some embodiments, the first and third pitches can be the same or different so long as the average pitch of the first and third portions 672, 676 is less than the average pitch of the second portion 674. Additionally, in some embodiments, the coil 670 or portions thereof can be made of or include a radiopaque or imaging material.

Figure 7:
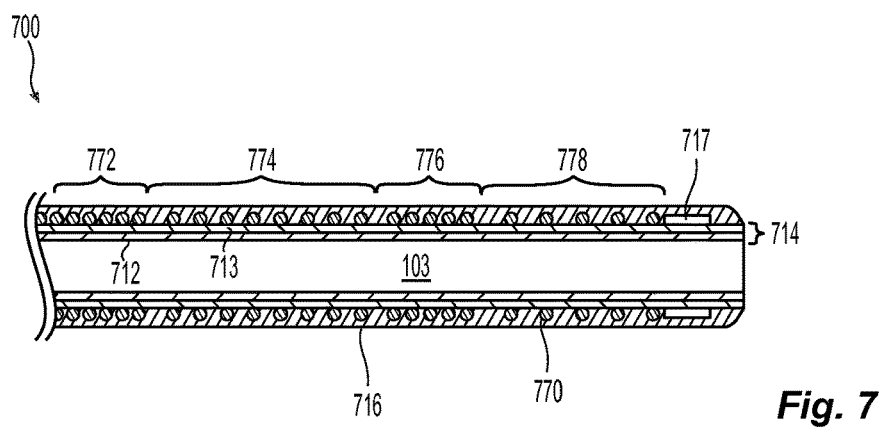
FIG. 7 is a cross-sectional side view of a distal portion of an elongated shaft configured in accordance with the present technology.

FIG. 7 is a cross-sectional side view of a distal portion 700 of a catheter shaft configured in accordance with the present technology. The distal portion 700 can include a radiopaque marker 717, an inner polymer structure 714, an outer polymer structure 716 surrounding at least a portion of the inner polymer structure 714, and a coil 770 wound around at least a portion of the inner polymer structure 714. In the embodiment shown in FIG. 7, the inner polymer structure 714 extends the length of the distal portion 700 such that the inner polymer structure 714 terminates distally at an opening 718 at the distal terminus of the distal portion 700. The inner polymer structure 714 defines a lumen that can be generally continuous with the lumen 103 of any of the shaft embodiments described above with reference to FIGS. 1A-2.

The inner polymer structure 714 can include a single layer of material or it can have two or more layers of the same or different materials. For example, as shown in FIG. 7, the inner polymer structure 714 can include a first layer 712 and a second layer 713 surrounding the first layer 712. As such, an inner surface of the first layer 712 defines the shaft lumen 103. The second layer 713 can be made of any of the materials described above with respect to the inner polymer structure 714. The first layer 712 can comprise a lubricious polymer such as HDPE or PTFE, for example, or platinum, PEEK, PE, PP, or a copolymer of tetrafluoroethylene, such as FEP, a copolymer of tetrafluoroethylene with perfluoroethers, such as PFA (more specifically, perfluoropropyl vinyl ether or perfluoromethyl vinyl ether), or the like. Moreover, in some embodiments the inner polymer structure 714 can be formed of a single layer (e.g., only the first layer 712, only the second layer 713, etc.), and in other embodiments the inner polymer structure 714 can include more than two layers (e.g., three layers, four layers) depending upon the desired characteristics of the device.

The outer polymer structure 716 directly contacts at least a portion of the inner polymer structure 714 and encases at least a portion of the coil 770. For example, in the embodiment shown in FIG. 7, at least a portion of the surface of the coil 770 directly contacts the second layer 713 of the inner polymer structure 714, while a remaining portion of the coil's surface directly contacts the outer polymer structure 716. In some embodiments the outer polymer structure 716 extends along the length of the distal portion 700 such that a distal terminus of the outer polymer structure 716 corresponds to the distal terminus of the distal portion 700. The outer polymer structure 716 (and/or portions thereof) can be made of any of the materials described above with respect to the outer polymer structure 116.

The coil 770 can be one or more round wires or flat ribbons helically wound around the inner polymer structure 714. The coil 770 can extend all or a portion of the length of the distal portion 700. For example, in the embodiment shown in FIG. 7, the coil 770 has a distal terminus that is aligned with or just proximal of the radiopaque marker 717, and the radiopaque marker 717 is proximal of the distal terminus of the distal portion 700. The pitch of adjacent turns of the coil 770 may be tightly wound so that each turn touches the succeeding turn or the pitch may be set such that the coil 770 is wound in an open fashion. The pitch of the coil 770 can be the same or vary along the length of the coil 770. For example, in the embodiment shown in FIG. 7, the coil 770 has a first portion 772, a second portion 774 distal of the first portion 772, a third portion 776 distal of the second portion 774, and a fourth portion 778 distal of the third portion 776. The first portion 772 has a first pitch, the second portion 774 has a second pitch greater than the first pitch, the third portion 776 has a third pitch less than the second pitch, and the fourth portion 778 has a fourth pitch greater than each of the first and third pitches. Accordingly, regions of the distal portion 700 corresponding to the first and third portions 772, 776 of the coil 770 are less flexible than regions of the distal portion 700 corresponding to the second and fourth portions 774, 778 of the coil 770.

In some embodiments, the first and third pitches can be generally the same, and the second and fourth pitches can be generally the same and greater than the first and third pitches. In other embodiments, the first and third portions 772, 776 can have the same and/or different pitches and/or the second and fourth portions 774, 778 can have the same and/or different pitches, so long as the average pitch of the first and third portions 772, 776 is less than the average pitch of the second and fourth portions 774, 778. Additionally, in some embodiments, the coil 770 or portions thereof can be made of or include a radiopaque or imaging material.

Figure 8:
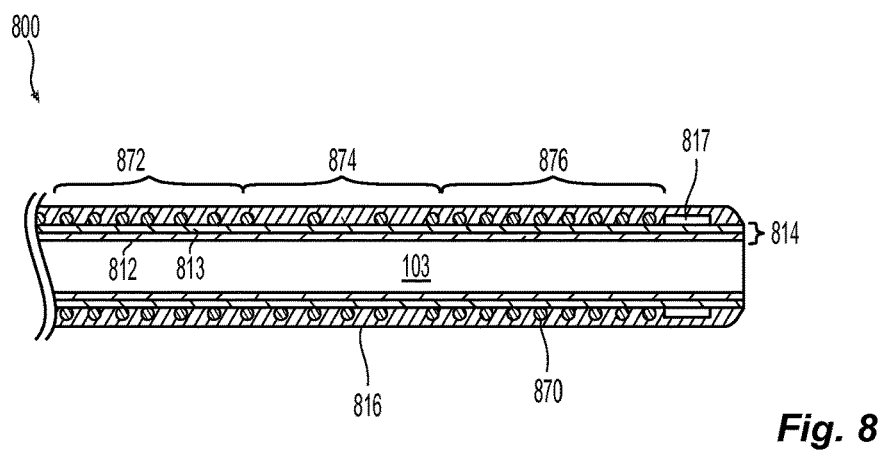
FIG. 8 is a cross-sectional side view of a distal portion of an elongated shaft configured in accordance with the present technology.

FIG. 8 is a cross-sectional side view of a distal portion 800 of a catheter shaft configured in accordance with the present technology. The distal portion 800 can include a radiopaque marker 817, an inner polymer structure 814, an outer polymer structure 816 surrounding at least a portion of the inner polymer structure 814, and a coil 870 wound around at least a portion of the inner polymer structure 814. In the embodiment shown in FIG. 8, the inner polymer structure 814 extends the length of the distal portion 800 such that the inner polymer structure 814 terminates distally at an opening 818 at the distal terminus of the distal portion 800. The inner polymer structure 814 defines a lumen that can be generally continuous with the lumen 103 of any of the shaft embodiments described above with reference to FIGS. 1A-2.

The inner polymer structure 814 can include two or more layers. For example, as shown in FIG. 8, the inner polymer structure 814 can include a first layer 812 and a second layer 813 surrounding the first layer 812. As such, an inner surface of the first layer 812 defines the shaft lumen 103. The second layer 813 can be made of any of the materials described above with respect to the inner polymer structure 814. The first layer 812 can comprise a lubricious polymer such as HDPE or PTFE, for example, or platinum, PEEK, PE, PP, or a copolymer of tetrafluoroethylene, such as FEP, a copolymer of tetrafluoroethylene with perfluoroethers, such as PFA (more specifically, perfluoropropyl vinyl ether or perfluoromethyl vinyl ether), or the like. Moreover, in some embodiments the inner polymer structure 814 can be formed of a single layer (e.g., only the first layer 812, only the second layer 813, etc.), and in other embodiments the inner polymer structure 814 can include more than two layers (e.g., three layers, four layers) depending upon the desired characteristics of the device.

The outer polymer structure 816 directly contacts at least a portion of the inner polymer structure 814 and encases at least a portion of the coil 870. For example, in the embodiment shown in FIG. 8, at least a portion of the surface of the coil 870 directly contacts the second layer 813 of the inner polymer structure 814, while a remaining portion of the coil's surface directly contacts the outer polymer structure 816. In some embodiments the outer polymer structure 816 extends along the length of the distal portion 800 such that a distal terminus of the outer polymer structure 816 corresponds to the distal terminus of the distal portion 800. The outer polymer structure 816 (and/or portions thereof) can be made of any of the materials described above with respect to the outer polymer structure 116.

The coil 870 can be one or more round wires or flat ribbons helically wound around the inner polymer structure 814. The coil 870 can extend all or a portion of the length of the distal portion 800. For example, in the embodiment shown in FIG. 8, the coil 870 has a distal terminus that is aligned with or just proximal of the radiopaque marker 817, and the radiopaque marker 817 is proximal of the distal terminus of the distal portion 800. The pitch of adjacent turns of the coil 870 may be tightly wound so that each turn touches the succeeding turn or the pitch may be set such that the coil 870 is wound in an open fashion. The pitch of the coil 870 can be the same or vary along the length of the coil 870. For example, in the embodiment shown in FIG. 8, the coil 870 has a first portion 872, a second portion 874 distal of the first portion 872, and a third portion 876 distal of the second portion 874. The first portion 872 has a first pitch, the second portion 874 has a second pitch greater than the first pitch, and the third portion 876 has a third pitch less than the second pitch. Accordingly, regions of the distal portion 800 corresponding to the first and third portions 872, 876 of the coil 870 are less flexible than a region of the distal portion 800 corresponding to the second portion 874 of the coil 870. In some embodiments, the first and third pitches can be the same or different so long as the average pitch of the first and third portions 872, 876 is less than the average pitch of the second portion 874. Additionally, in some embodiments, the coil 870 or portions thereof can be made of or include a radiopaque or imaging material.

In the embodiment shown in FIG. 8, the coil 870 has a first portion 872 having a first pitch, a second portion 874 having a second pitch greater than the first pitch, and a third portion 876 have a third pitch less than the second pitch. The first and third pitches can be the same or different. The third portion 876 can be distal of the second portion 874, and the second portion 874 can be distal of the first portion 872.

III. SELECTED METHODS OF MANUFACTURE

The outer polymer structure 116 can be constructed and disposed using any appropriate technique, for example, by extrusion, co-extrusion, ILC, coating, heat shrink techniques, heat bonding, casting, molding, fusing one or several segments of an outer polymer structure material end-to-end, or the like. The outer polymer structure 116 can be secured to the inner polymer structure 114, the coil 170, the inner braid 160, and/or the outer braid 162 by any of the above techniques. In embodiments where the outer polymer structure 116 is constructed independently of the other portions of the shaft 106, the outer polymer structure 116 may be thereafter secured to the inner polymer structure 114, the inner braid 160, the outer braid 162, and/or the coil 170 using suitable techniques such as adhesive bonding, crimping, friction fitting, mechanically fitting, chemically bonding, thermally bonding, welding (e.g., resistance, RF, or laser welding), soldering, brazing, or the use of a connector member or material, or the like, or combinations thereof.

IV. CONCLUSION

Several other embodiments of the technology can have different states, components, or procedures than those described herein. Moreover, it will be appreciated that specific elements, substructures, advantages, uses, and/or other features of the embodiments described with reference to FIGS. 1A-8 can be suitably interchanged, substituted or otherwise configured with one another in accordance with additional embodiments of the present technology. For example, any of the distal portions described with reference to FIGS. 3-8 can be combined with any of the elongated shafts and/or catheter systems described with references to FIGS. 1A-2. Furthermore, suitable elements of the embodiments described with reference to FIGS. 1A-8 can be used as standalone and/or self-contained devices. A person of ordinary skill in the art, therefore, will accordingly understand that the technology can have other embodiments with additional elements, or the technology can have other embodiments without several of the features shown and described above with reference to FIGS. 1A-8.

Although the invention has been described in terms of particular embodiments and applications, one of ordinary skill in the art, in light of this teaching, can generate additional embodiments and modifications without departing from the spirit of or exceeding the scope of the exampled invention. Accordingly, it is to be understood that the drawings and descriptions herein are proffered by way of example to facilitate comprehension of the invention and should not be construed to limit the scope thereof.

We claim:

1. A catheter comprising:
   an elongated shaft having a proximal portion, a distal portion, and an intermediate portion therebetween, wherein the distal portion terminates distally at an opening;
   wherein:
   the intermediate portion has a proximal region, an overlapping region, and a distal region, the overlapping region being between the proximal and distal regions;
   the proximal region extends from the proximal portion of the shaft to the overlapping region;
   the proximal region includes an inner polymer structure, an outer polymer structure, an inner braid, and an outer braid surrounding the inner braid;
   the outer polymer structure is disposed in and around the inner braid and the outer braid;
   the inner braid comprises a first plurality of interwoven wires;

the outer braid comprises a second plurality of interwoven wires;

the overlapping region extends from the proximal region to the distal region;

the overlapping region includes: (a) the inner polymer structure, (b) the outer polymer structure, (c) a coil wound around the inner polymer structure and positioned within the outer polymer structure, and (d) the outer braid;

a proximal terminus of the coil is at a border between the proximal region and the overlapping region;

a distal terminus of the inner braid is at the border between the proximal region and the overlapping region;

a distal terminus of the outer braid is at a border between the overlapping region and the distal region;

the distal region extends from the overlapping region to the distal portion;

the distal region includes the inner polymer structure, the outer polymer structure, and the coil wound around at least a portion of the inner polymer structure and does not include the inner braid or the outer braid;

a pitch of the coil is less at a distal region of the coil than at a proximal region of the coil.

2. The catheter of claim 1, wherein a stiffness of the inner polymer structure decreases in a distal direction.

3. The catheter of claim 1, wherein a stiffness of the outer polymer structure decreases in a distal direction.

4. The catheter of claim 1, wherein the outer polymer structure has a first section having a first stiffness and a second section distal to the first section having a second stiffness less than the first stiffness.

5. The catheter of claim 1, wherein an outer diameter of the shaft at the distal region is less than an outer diameter of the shaft at the overlapping region.

6. The catheter of claim 1, wherein the outer polymer structure is composed of two different polymers.

7. The catheter of claim 1, wherein the outer polymer structure is composed of three different polymers.

8. The catheter of claim 1, wherein the outer polymer structure is composed of four different polymers.

9. The catheter of claim 1, further comprising a handle coupled to the proximal portion of the shaft.

10. The catheter of claim 1, further comprising a liner that coats an inner surface of the inner polymer structure.

11. The catheter of claim 1, further comprising a radiopaque marker positioned along the distal portion distal of a distal terminus of the coil.

12. The catheter of claim 1, wherein the pitch of the coil varies along a length of the coil.

13. The catheter of claim 1, wherein the inner braid has an inner braid pitch, and wherein the inner braid pitch is constant along a length of the inner braid.

14. The catheter of claim 1, wherein the outer braid has an outer braid pitch, and wherein the outer braid pitch is constant along a length of the outer braid.

15. The catheter of claim 1, wherein the inner braid, the outer braid, and the coil are embedded in the outer polymer structure.

16. The catheter of claim 1, wherein the inner polymer structure comprises a first layer and a second layer surrounding the first layer.

17. The catheter of claim 16, wherein the second layer ends proximal of a distal terminus of the coil.

* * * * *